United States Patent [19]

Batyrev et al.

[11] 4,264,207
[45] Apr. 28, 1981

[54] METHOD AND APPARATUS FOR DETERMINING THE QUALITY OF ORIENTED POLYMERIC MATERIALS

[76] Inventors: Ruslan I. Batyrev, Vadkovsky pereulok, 24, kv. 23; Semen I. Gdalin, Oktyabrskaya ulitsa, 19, kv. 79; Boris F. Zaretsky, Maisky pereulok, 16, kv. 71; Vladimir E. Terekhin, 2 Filevskaya ulitsa, 13, kv. 29; Valentin G. Semenov, Rossoshanskaya ulitsa, 7, korpus 1, kv. 1; Viktor V. Malinin, Deguninskaya ulitsa, 22, kv. 75; Jury V. Popov, Petrozavodskaya ulitsa, 5, kv. 452; Alexandr S. Kechekian, Levshinsky pereulok, 14/9, kv. 31, all of Moscow, U.S.S.R.

[21] Appl. No.: 36,176

[22] Filed: May 4, 1979

[51] Int. Cl.³ .............................................. G01J 4/00
[52] U.S. Cl. ...................................... 356/364; 356/369
[58] Field of Search ................. 356/369, 367, 364, 338

[56] References Cited

U.S. PATENT DOCUMENTS

| 2,824,488 | 2/1958 | Bridges et al. | 356/367 |
|---|---|---|---|
| 3,904,293 | 9/1975 | Gee | 356/369 |
| 4,037,965 | 7/1977 | Weiss | 356/338 |

OTHER PUBLICATIONS

Rogovin, et al., "New Investigation Methods for Polymers", (Extract), "Mir" Publishers, Moscow, 1968, p. 24.

*Primary Examiner*—Bruce C. Anderson
*Attorney, Agent, or Firm*—Lackenbach, Lilling & Siegel

[57] ABSTRACT

A method of determining the quality of oriented polymeric materials, based on the effect of small-angle scattering, comprises the passage of a beam of monochromatic, polarized and collimated light through a given material, extracting the scattered reflections, converting them to a train of electric pulses, and determining the degree of orientation of the material using the pulse spacing. An apparatus for determining the quality of oriented polymeric materials comprises a source which produces monochromatic, polarized and collimated light passed through an oriented polymeric material, and a housing which accommodates an analyzer, a mask and a scattered reflection converting unit to convert the scattered reflections extracted by the mask to a train of electric pulses, which are arranged serially along the direction of the light beam after the material. The scattered reflection converting unit comprises a scattered light detector coupled to the recorder.

9 Claims, 6 Drawing Figures

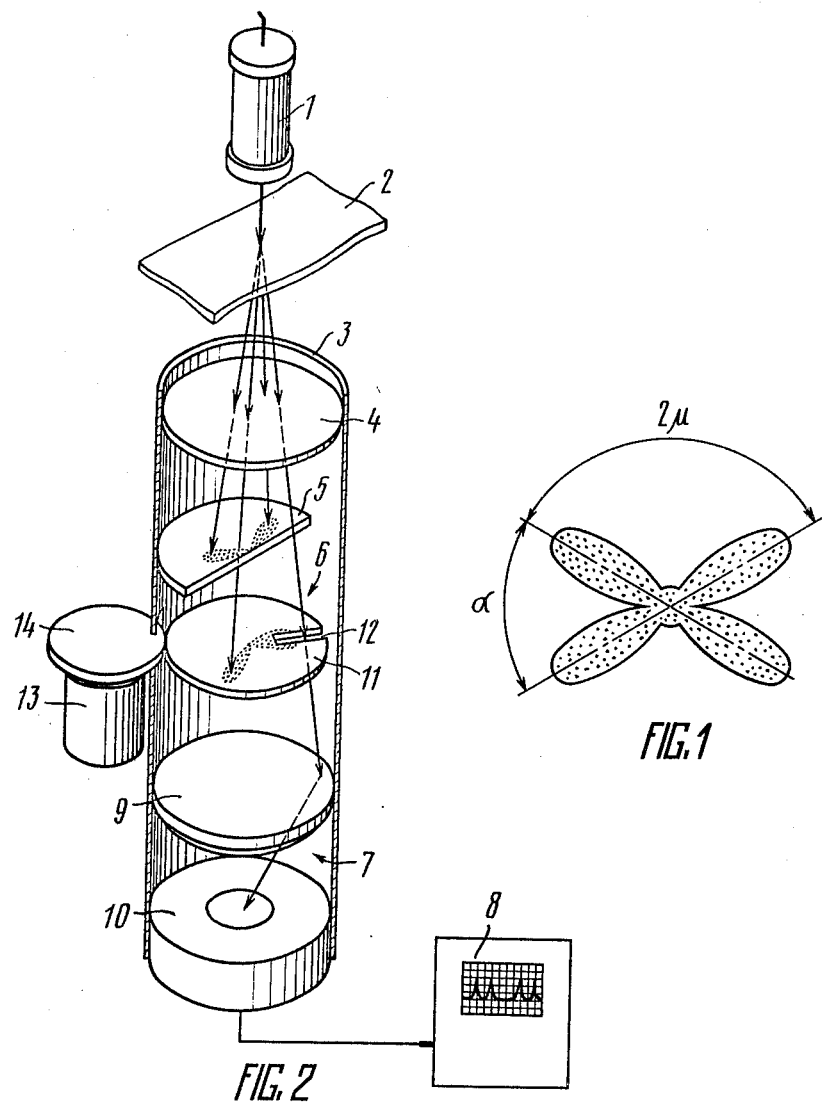

4,264,207

METHOD AND APPARATUS FOR DETERMINING THE QUALITY OF ORIENTED POLYMERIC MATERIALS

FIELD OF THE INVENTION

The invention relates to production methods for polymeric materials, and more particularly to methods and devices for determining the quality of polymeric materials.

The method and apparatus of the invention can find use in chemical, textile and other industries utilizing oriented polymeric materials such as films, fibers, tubings, sheets and the like. Other applications are concerned with the measurement of stresses that occur in polymeric materials.

DESCRIPTION OF THE PRIOR ART

At present, polymeric materials are manufactured on a wide basis, having an oriented structure in order to improve their physical/mechanical properties, including strength, flexibility, transparency and others. The properties of commercial polymeric materials are tested in laboratories by using tensile testing machines which handle previously cut samples. Such methods cannot allow for effective control of production processes and specialists therefore seek to provide new testing techniques capable of measuring the quality of polymeric materials during their manufacture and compatible with the control scheme for the given production process.

The prior art knows a method of determining the quality or oriented polymeric materials (cf. a book entitled "New Investigation Methods for Polymers", a collection of translations and reviews ed. by Z. A. Rogovin and V. P. Zubov, "Mir" Publishers, Moscow, 1968, p. 24), based on the effect of small-angle scattering of polarized light and involving the passage of a beam of monochromatic, polarized and collimated light through a given material and the extraction of the scattered reflections. The intensity of scattered light is measured at different points of a scattered reflection pattern for different positions of the vector of orientation of the specimen under investigation and the measurement results are then processed to determine the characteristics of the specimen.

Known in the art is an apparatus for determining the quality of oriented polymeric materials, comprising a source that produces a beam of monochromatic, polarized and collimated light passed through a given specimen, and a housing which accommodates an analyzer and a scattered light detector, serially arranged along the direction of the light beam after the specimen, said scattered light detector being coupled to a recorder. In the known apparatus, the specimen is fixed to a stand which can be rotated in a plane at right angles to the light beam axis which constitutes the axis of revolution of the stand. The scattered light detector is positioned after the specimen and can be rotated about the vertical axis of the specimen. The intensity of the scattered light at different points of a scattered reflection pattern is detected and is then converted to an electric signal applied to a recorder.

The described method can determine the intensity of scattered light only, which is an ambiguous parameter and cannot therefore provide, without further analysis, for a measure of physical/mechanical properties of the finished material.

The known apparatus is a laboratory one and can measure automatically only the intensity of scattered light at different points of a scattered reflection pattern. With this apparatus it is impossible, however, to measure other parameter concerned with small-angle scattering or conduct measurements in the case of linear movement of the specimen. As a result, the apparatus cannot be coupled with the production equipment and cannot therefore provide for continuous measurements which would ensure automatic control of the production process.

SUMMARY OF THE INVENTION

An object of the invention is to provide a method for determining the quality of oriented polymeric materials, whereby the magnitude of a single characteristic is measured automatically during the manufacture of a given material.

Another object of the invention is to provide an apparatus for determining the quality of oriented polymeric materials, whereby the magnitude of the quality characteristic is registered automatically and the production process can be therefore controlled.

The invention therefore seeks to provide a method for determining the quality of oriented polymeric materials, based on the effect of small-angle scattering of polarized light and involves the passage of a beam of monochromatic, polarized and collimated light through a given material and the extraction of the scattered reflection. The method comprises, according to the invention, converting the scattered reflections to a train of electric pulses and determining the extent of orientation of the material using the pulse spacing.

The invention therefore seeks to provide an apparatus for determining the quality of oriented polymeric materials, comprising a source that produces a beam of monochromatic, polarized and collimated light passing through an oriented polymeric material, and a housing which accommodates an analyzer and a scattered light detector serially arranged along the direction of the light beam after the material, the detector being coupled to a recorder, which apparatus comprises, according to the invention, installed directly after the analyzer as viewed in the direction of the light beam, a mask to extract the scattered reflections and a scattered reflection converting unit to convert the scattered reflections to a train of electric pulses.

Advantageously, the apparatus should comprise a rotatable diaphragm having its center coinciding with the axis of the light beam, and having at least one off-center hole, said diaphragm being part of the scattered light detector to constitute together with it the scattered reflection converting unit.

Preferably, the apparatus should comprise at least one rotatable off-center scattered light detector having its axis of revolution coinciding with the beam axis and constituting the scattered reflection converting unit.

Advantageously, the apparatus should comprise another diaphragm whose center constitutes a round hole, and a code disc disposed between the mask and the diaphragm and kinematically connected with the latter, said code disc having at least one off-center round hole whose axis is spaced from the axis of revolution of the disc by a distance equal to the distance between the axis of the disc and the beam axis.

Preferably, the apparatus should comprise a collimated beam source disposed between the mask and the first diaphragm and rigidly mounted within the housing, said source having its axis arranged in parallel with the axis of the beam produced by the source of monochromatic, polarized and collimated light.

Advantageously, the off-center hole in the first or the second diaphragm is made in the form of a circle, a segment, or a radially shaped slit.

The method of the invention can determine automatically the degree of orientation of an oriented polymeric material as a quantitatively represented quality characteristic. Since the degree of orientation of the material provides a unique relation to the physical/mechanical characteristics of the material during its manufacture, the production processes thereof can be controlled and an optimum magnitude of the quality characteristic is thus obtained.

The apparatus of the invention offers a simple design, provides for highly accurate measurements during the manufacture of the material, and for automatic control of the associated production process, with the result that the finished product has a higher quality.

DESCRIPTION OF THE ACCOMPANYING DRAWINGS

The invention will now be described in more detail, by way of example, with reference to the accompanying drawings of which FIG. 1 is a scattered reflection pattern;

FIG. 2 shows an apparatus for passing a beam of light utilizing a rotating diaphragm;

DESCRIPTION OF THE INVENTION

Figure 3:
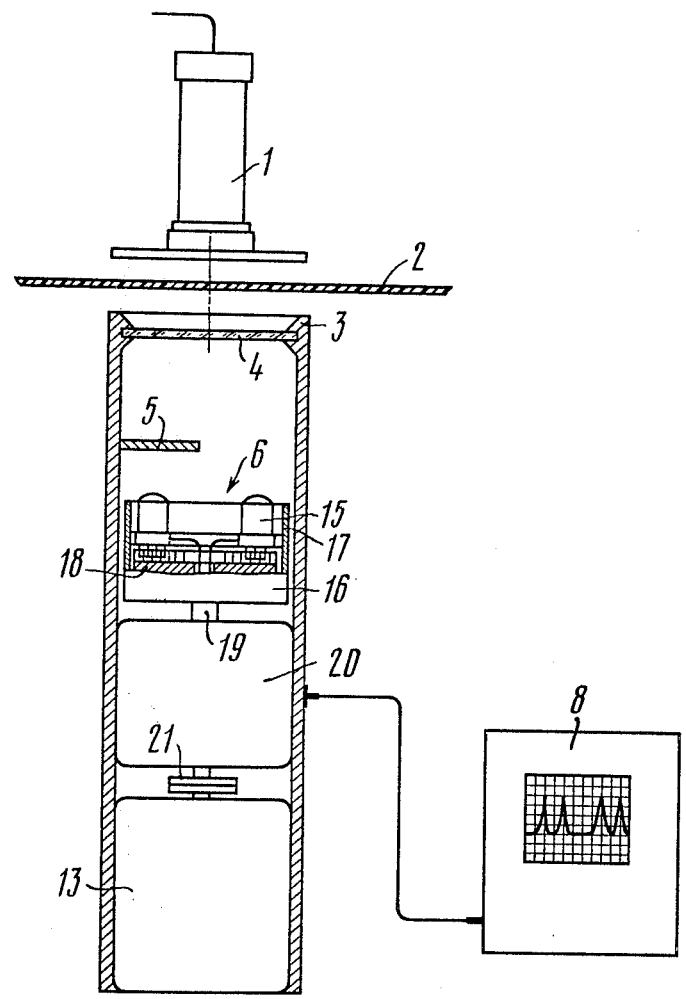
FIG. 3 shows another apparatus embodiment utilizing two light detectors.

The method of the invention comprises passing a beam of monochromatic, polarized and collimated light through a given oriented polymeric material, extracting the scattered reflections, converting the latter to a train of electric pulses, and determining the degree of orientation of the material using the pulse spacing.

The passage of the above-mentioned beam of light through the material produces a scattered reflection pattern shown in FIG. 1. The value of an obtuse angle $2\mu$ (doubled azimuth angle) between the scattered reflections is proportional to the value of optical anisotropy and of the degree of orientation of a given oriented polymeric material. The angles of 90° and 180°, respectively, are characteristic of completely nonoriented and completely oriented polymeric materials. In the case of converting the scattered reflection pattern to a train of electric pulses, the magnitudes of the doubled azimuth angle $2\mu$ and its adjoining angle $\alpha$ correspond to the pulse spacing. Either of these magnitudes or their relationship can serve as a measure of the degree of orientation of the material.

The degree of orientation therefore provides a means of determining physical/mechanical characteristics of the material, such as modulus of elasticity, strength limit and others.

The apparatus of the invention comprises a source 1 (FIG. 2) that produces a beam of monochromatic, polarized and collimated light passed through an oriented polymeric material 2, for example, a film made of polypropylene, polystyrene or the like. According to the given embodiment, the source 1 is a laser, though use may be made of any other source of monochromatic, polarized and collimated light, for example, a mercury lamp provided with collimating, diaphragm and polaroid means. Installed in a housing 3 after the film 2 is a serial arrangement, as viewed in the direction of the light beam shown by an arrow, including an analyzer 4, a mask 5, and a scattered reflection converting unit 6 which converts the scattered reflections extracted by the mask 5 to a train of electric pulses. The unit 6 comprises a scattered light detector 7 coupled to a recorder 8. The detector 7 includes a focusing lens 9 and an electronic multiplier 10. In the given embodiment, use may be made of any other focusing system comprised of different types of light cells, photosensitive diodes, light transistors and the like.

The analyzer 4 is a polaroid. The mask 5 is a plate in the form of a semi-circle. It also may be in the form of a circle having a number of holes of different shapes to provide for a suppression of interference resulting from defects of polymeric films, from optical components of the apparatus, from surrounding light sources, and from inaccuracy of the relative position of certain components of the apparatus. The optical axis of the apparatus is held in coincidence with the light beam axis, while the planes of the film 2, the analyzer 4, the mask 5 and the components of the unit 6 are at right angles to the light beam axis.

In the given embodiment, there is provided a rotatable diaphragm 11 having its center coinciding with the light beam axis, and having at least one off-center hole 12 which can be given different shapes. The diaphragm 11 consitutes, together with the detector 7, the scattered reflection converting unit 6. The diaphragm 11 is rotated by virtue of an electric motor 13 and a driving disc 14. Any other drive means can be used and the diaphragm 11 itself can constitute a rotor of an electric motor. In the given embodiment, the diaphragm 11 has a hole 12 in the form of a radially shaped slit. There may be more than one hole 12, a feature providing an increase in the scanning speed for the scattered reflection pattern, an increase in the light flux incident on the detector 7, and a compensation for an error resulted from inaccuracy of positioning certain components of the apparatus. The recorder 8 is an oscilloscope; on the other hand, any other voltmeter, digital or analog, operated in conjunction with an electronic converter, can be used. Described on the surfaces of the mask 5 and the diaphragm 11 are diagrammatic representations of a scattered reflection pattern.

Another embodiment of the apparatus of the invention includes at least one rotatable off-center scattered light detector 15 (FIG. 3). Here, two detectors 15 are available which have their axis of revolution in coincidence with the light beam axis and which serve as the scattered reflection converting unit 6. The detectors 15 are mounted in a rotatable barrel 16 comprised of a guide member 17 and a driving spiral member 18 which provide for radial movement of the detectors. The barrel 16 is mounted on a shaft 19 of a current-collecting means 20. The entire system is rotated by virtue of an electric motor 13 and a clutch 21. In this embodiment, the material 2 is a terilene fiber.

According to a still another embodiment of the invention, the apparatus comprises a diaphragm 22 (FIG. 4) whose center constitutes a round hole 23, a code disc 24 being kinematically coupled with the diaphragm 22 and installed between the latter and the mask 5. The code disc 24 has at least one off-center round hole 25 whose axis is spaced from the axis of revolution of the code disc 24 by a distance equal to the distance between the axis of the code disc 24 and the light beam axis. In the given embodiment, there is one hole 25. The code disc 24 produces a reading prepare pulse applied to the recorder 8. Gears 26, 27 provide for a kinematic connection between the code disc 24 and the diaphragm 22. According to the given embodiment, the material 2 is a terilene fiber.

Figures 4, 5:
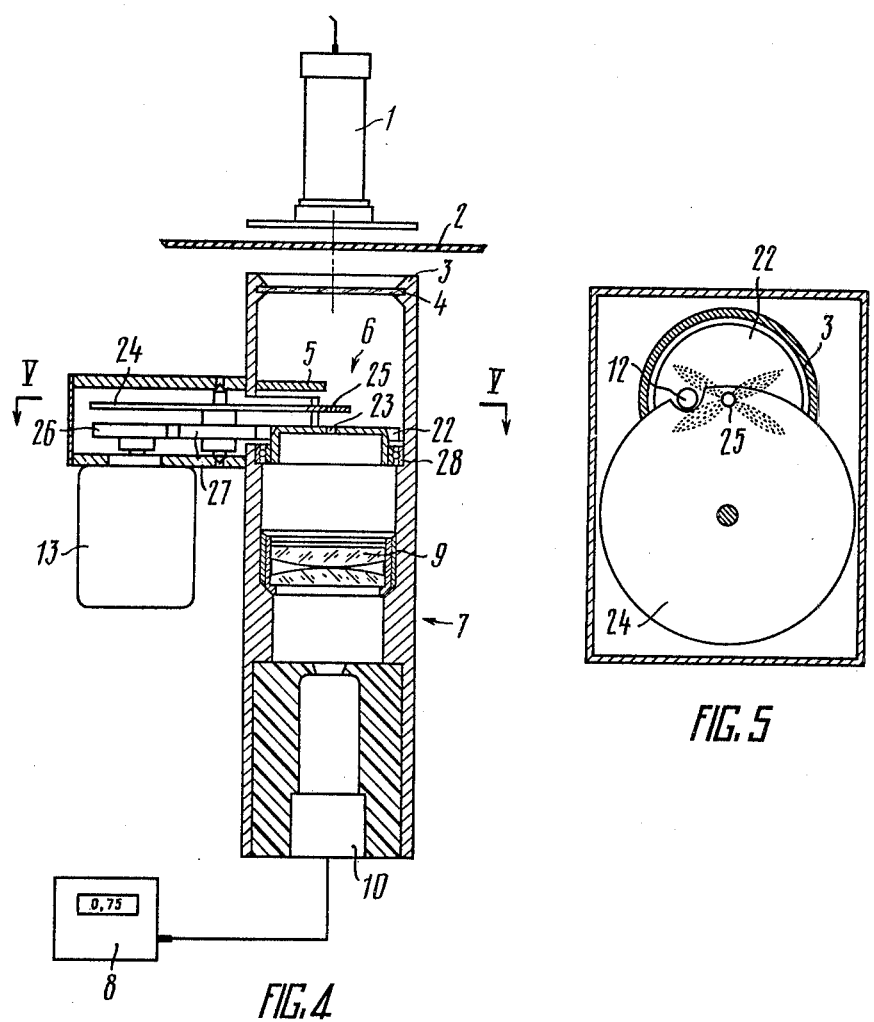
FIG. 4 shows another apparatus embodiment utilizing a diaphragm kinematically coupled to a code disc.
FIG. 5 is a sectional view of FIG. 4 along the lines V—V.

FIG. 5 shows a relative position of the diaphragm 22, having one round hole 12, and the code disc 24 at the point time when a reading prepare pulse is applied.

Described on the surfaces of the diaphragm 22 and the code disc 24 are diagrammatic representations of a scattered reflection pattern.

Figure 6:
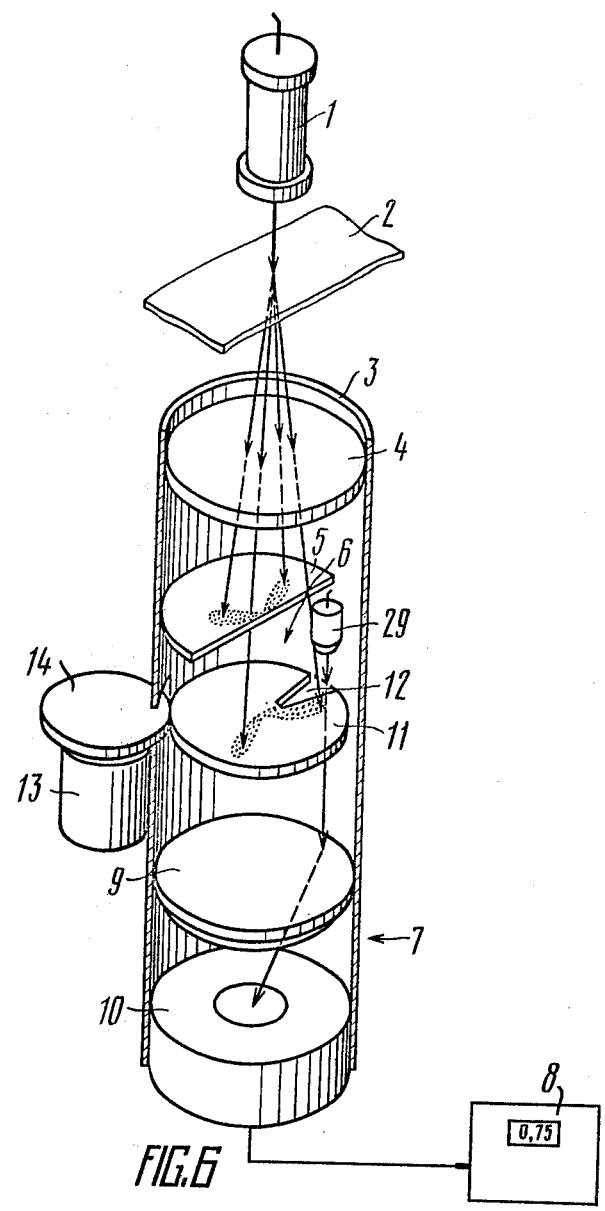
FIG. 6 is an apparatus embodiment utilizing a photosensitive diode as the beam source.

Yet another embodiment of the apparatus of the invention (FIG. 6) deals with a collimated beam source 29 disposed between the mask 5 and the diaphragm 11 and rigidly mounted in the housing 3. The source 29 has its axis maintained in parallel with the axis of a beam produced by the source 1. According to the given embodiment, the source 29 is a photosensitive diode, but any other collimated beam source can be used. FIG. 6 shows the apparatus at the point in time a reading prepare pulse from the source 29 is applied to the electronic multiplier 10. Described on the surfaces of the mask 5 and the diaphragm 11 are diagrammatic representations of a scattered reflection pattern. The hole 12 in the diaphragm 11 has the shape of a segment. Note that the shape of the hole 12 may be a circle, a segment, or a radially shaped slit, depending on the type of a polymer being investigated and on the requirements imposed on the accuracy and range of measurements.

The apparatus of the invention operates in the following manner. The source 1 (FIG. 2) produces a beam of monochromatic, polarized and collimated light that passes through the material 2, for example, a polymeric film, and is subject to a partial scattering, with the result that a scattered reflection pattern (FIGS. 1, 2) is formed. Depending on the position of the vector of polarization of the analyzer 4 relative to the vector of beam polarization, the analyzer 4 extracts the component $V_V$ or $H_V$ from the scattered reflection pattern. In addition, the analyzer 4 and mask 5 operate to reject interference signals resulting from the defects of the film 2 and from other light sources. The light beam provided by the scattered reflections is then incident on the rotatable diaphragm 11 which, when rotated by the electric motor 13 and driving disc 14, produces the light beam pulses at the points in time when the hole 12 passes by the scattered reflections. These pulses impinge through the focusing lens 9 on to the electronic multiplier 10 which converts them to a train of electric pulses presented to the recorder 8. The spacing of the electric pulses is proportional to the magnitude of the doubled azimuth angle in a range of $90° \leq 2\mu \leq 180°$ and to the magnitude of the angle $\alpha$ adjacent that doubled azimuth angle and having a range of $90° \geq \alpha \geq 0°$.

In the embodiment including two detectors 15 (FIG. 3), the light flux provided by the scattered reflections impinges alternately on each of the detectors and is converted to a train of electric pulses. With two detectors 15 and with the mask 5 having the shape of a semicircle, the pulse rate is increased by a factor of 2. On the other hand, with two detectors 15 and with the mask 5 in the form of a circle having segment-shaped holes, an inequality of the light fluxes from the scattered reflections, resulting from a condition in which the plane of the film 2 is not at right angles to the light beam from the source 1, is compensated. A radial movement of the detectors 15, attained through the agency of the guide member 17 and driving spiral member 18, makes it possible to scan different portions of the scattered reflection pattern, a feature providing for flexibility of operation in handling different polymeric materials.

When the apparatus of the invention operates in conjunction with digital or analog equipment, an error of reading the angle $\alpha$ adjacent the doubled azimuth angle $2\mu$ is likely to occur. To eliminate that error, a reading prepare light signal applied to the detector 7 produces an electric pulse which has an amplitude considerably different from the amplitude of the scattered reflection signals. The reading prepare light signal is provided by the code disc 24 (FIG. 4) having the hole 25 and by the central hole 23 in the diaphragm 22. During the rotation of the code disc 24 (FIG. 5) and of the diaphragm 22, a point in time is reached at which the hole 12 of the diaphragm 22 passes by the horizontal axis of the scattered reflection pattern. At that point in time, the hole 25 of the code disc 24 is brought into coincidence with the central hole 23 and a nonscattered light beam from the source 1 (FIG. 4) impinges on the electronic multiplier 10. Since the nonscattered light has a considerably greater intensity as compared with the intensity of the scattered reflections, the amplitude of the pulse provided by the reading prepare signal is of a greater value, with the result that the recorder 8 is allowed to take a reading.

To eliminate the reading error of the angle $\alpha$, the collimated beam source 29 (FIG. 6) produces a reading prepare light signal. The source 29 is so positioned that the axis of its light beam is held in parallel with the axis of the light beam from the source 1, and in coincidence with the horizontal axis of the scattered reflection pattern. When the hole 12 of the diaphragm 11 intersects the horizontal axis of the horizontal axis of the scattered reflection pattern, the light from the source 29 impinges on to the electronic multiplier 10, said light having an intensity considerably greater than that of the light obtainable from the scattered reflections.

Given below is an example illustrating the method of the invention, when the degree of orientation of a polypropylene film 60μm thick is determined. To this end, the source 1 (FIG. 6), which is a 6328-Å gaseous laser, produces a light beam which is subject to scattering after the passage through the film 2. A photosensitive diode is used as the collimated beam source 29. The speed of revolution of the diaphragm 11 amounts to 3000 r.p.m. The light pulses from the photosensitive diode and from the scattered reflections are incident on the electronic multiplier 10 which produces a train of electric pulses having a pulse spacing in a range of 5 to 10 ms, which corresponds to the doubled azimuth angle $2\mu$, and a pulse spacing in a range of 5 to 0 ms, which corresponds to the angle $\alpha$. The electric pulses have a 5-V amplitude. The reading prepare pulse provided by the photosensitive diode and followed by two successive pulses, which are spaced by an interval corresponding to the doubled azimuth angle $2\mu$, has a 10-V amplitude. The train of electric pulses is applied to the input of the digital recorder 8. The input unit of the latter can be enabled or disabled by using 5-V pulses only after the passage of a 10-V pulse. Thus, one can read only a digital reading of a time interval corresponding to the doubled azimuth angle $2\mu$ during continual measurement of the degree of orientation of the moving polymeric material, for example, a film.

The method and apparatus of the invention provide a reliable and simple means of determining the quality characteristic of an oriented polymeric material when it is being processed on the production equipment. When inserted in an automatic control system for the given production process, the apparatus of the invention can influence the production process using the measurement data, thereby providing oriented polymeric materials possessing optimum physical/mechanical properties.

What is claimed is:

1. A method for determining the degree of orientation of a polymeric material as a means for determining its quality, comprising:
    passing a beam of monochromatic, polarized and collimated light through a given polymeric material to produce a scattered reflection pattern;
    extracting components of the scattered reflection pattern by means of a polaroid analyzer and a mask located sequentially; converting the extracted components to a train of electric pulses; and
    determining the degree of orientation of the polymeric material from the spacing of the electric pulses.

2. An apparatus for determining the quality of oriented polymeric materials, comprising a source which produces a beam of monochromatic, polarized and collimated light passing through an oriented polymeric material;
    a housing arranged along the direction of the light beam and located after said polymeric material;
    a polaroid analyzer mounted in said housing;
    a mask mounted in said housing and arranged along the light beam located after said analyzer;
    a scattered reflection pattern converting unit to convert components of the scattered reflection pattern extracted by the mask to a train of electric pulses, said unit being located in said housing along the light beam after said mask and being provided with a scattered light detector;
    a recorder connected to said scattered light detector.

3. An apparatus as claimed in claim 2, comprising a rotatable diaphragm with its center coinciding with the axis of the beam, and having at least one off-center hole, said diaphragm being part of the scattered light detector to constitute together with it said scattered reflection converting unit.

4. An apparatus as claimed in claim 2, comprising at least one rotatable off-center scattered light detector having its axis of revolution coinciding with the axis beam and constituting the scattered reflection converting unit.

5. An apparatus as claimed in claim 3, comprising another diaphragm, whose center constitutes a round hole, and a code disc disposed between the mask and said first diaphragm and kinematically connected with the latter, said disc having at least one off-center round hole whose axis is spaced from the axis of revolution of the disc by a distance equal to the distance between the axis of the disc and the beam axis.

6. An apparatus as claimed in claim 3, comprising a collimated beam source disposed between the mask and said first diaphragm and rigidly mounted within the housing, said source having its axis arranged in parallel with the axis of the beam produced by the source of monochromatic, polarized and collimated light.

7. An apparatus as claimed in claim 3, wherein said hole of said diaphragm is made in the form of a circle, a segment, or a radial slit.

8. An apparatus as claimed in claim 5, wherein said hole of said diaphragm is made in the form of a circle, a segment, or a radial slit.

9. An apparatus as claimed in claim 6, wherein said hole of said diaphragm is made in the form of a circle, a segment, or a radial slit.

* * * * *